(12) United States Patent
Münchmeyer et al.

(10) Patent No.: US 8,866,072 B2
(45) Date of Patent: Oct. 21, 2014

(54) METHOD AND APPARATUS FOR DETECTING AND IDENTIFYING GASES BY MEANS OF ION MOBILITY SPECTROMETRY

(75) Inventors: Wolf Münchmeyer, Ehra-Lessien (DE);
Bert Ungethüm, Schwerin (DE);
Andreas Walte, Schwerin (DE)

(73) Assignee: Airsense Analytics GmbH, Schwerin (DE)

( * ) Notice: Subject to any disclaimer, the term of this patent is extended or adjusted under 35 U.S.C. 154(b) by 0 days.

(21) Appl. No.: 13/820,890

(22) PCT Filed: Aug. 11, 2011

(86) PCT No.: PCT/EP2011/063804
§ 371 (c)(1),
(2), (4) Date: Mar. 5, 2013

(87) PCT Pub. No.: WO2012/034795
PCT Pub. Date: Mar. 22, 2012

(65) Prior Publication Data
US 2013/0161509 A1 Jun. 27, 2013

(30) Foreign Application Priority Data
Sep. 14, 2010 (EP) .................................. 10176538

(51) Int. Cl.
*H01J 49/00* (2006.01)
*G01N 27/62* (2006.01)

(52) U.S. Cl.
CPC .................................. *G01N 27/622* (2013.01)
USPC ............ 250/282; 250/281; 250/290; 250/292

(58) Field of Classification Search
USPC .................................. 250/281, 282, 290, 292
See application file for complete search history.

(56) References Cited

U.S. PATENT DOCUMENTS

| 4,445,038 A | 4/1984 | Spangler et al. |
| 6,124,592 A * | 9/2000 | Spangler ........................ 250/287 |

(Continued)

FOREIGN PATENT DOCUMENTS

| GB | 2 228 139 A | 8/1990 |
| WO | 03/005014 A1 | 1/2003 |

(Continued)

OTHER PUBLICATIONS

International Search Report Dated Oct. 31, 2011, Mailed Jan. 4, 2012.
G.A. Eiceman and Z. Karpas "Ion Mobility Spectrometry", (2nd. edition, CRC, Boca Raton, 2005).
Rokushika, Hatano, Baim und Hill Rokushika S., Hatano H., Baim M.A., Hill H.H., "Resolution Measurement for Ion Mobility Spectrometry", Anal. Chem. 1985, 57, 1902.

* cited by examiner

*Primary Examiner* — Michael Maskell
(74) *Attorney, Agent, or Firm* — Norris McLaughlin & Marcus PA

(57) ABSTRACT

The invention relates to a method for identifying gases, which are ionized and the drift times of the positive and negative product ions through drift spaces are measured and the measured drift times are evaluated, wherein for measuring the drift times the product ions are accelerated to drift velocities by a resulting electrical field. It is provided that the positive and negative product ions move synchronously and in parallel in the same direction.

The invention further relates to a device for identifying gases, which includes at least two drift tubes, wherein each of the drift tubes has at least one respective detector for detecting product ions. For this purpose, at least two drift tubes are arranged in parallel next to each other and are delimited, on one hand, by a common inlet system and, on the other hand, by at least one detector.

8 Claims, 1 Drawing Sheet

(56) References Cited

U.S. PATENT DOCUMENTS 6,459,079 B1 * 10/2002 Machlinski et al. .......... 250/286
2005/0006578 A1 * 1/2005 Rockwood et al. .......... 250/289
2007/0040111 A1 2/2007 Jill et al.
2007/0228269 A1 * 10/2007 Miller et al. .................. 250/282

FOREIGN PATENT DOCUMENTS

| | | |
|---|---|---|
| WO | 2005/001464 A1 | 1/2005 |
| WO | 2008/107640 A1 | 9/2008 |

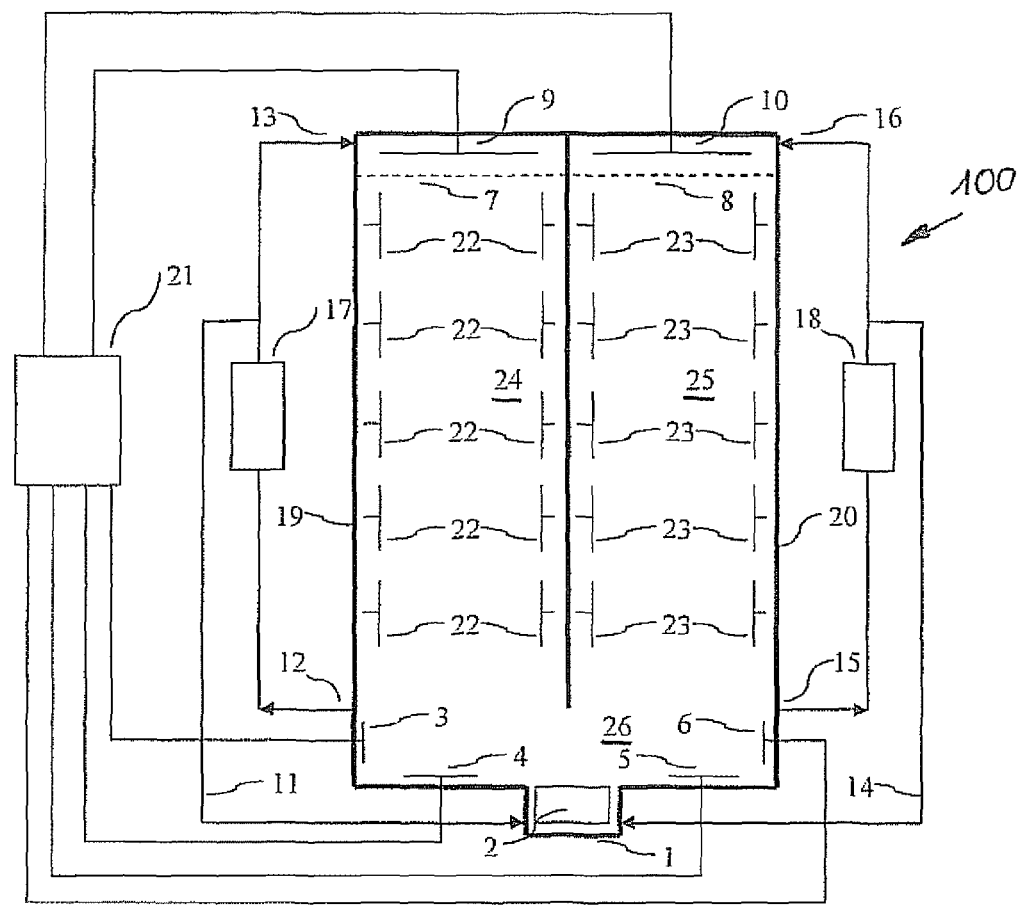

METHOD AND APPARATUS FOR DETECTING AND IDENTIFYING GASES BY MEANS OF ION MOBILITY SPECTROMETRY

The invention relates to a method and a device for identifying gases.

Such methods and the associated devices for detecting and identifying gases are used for detecting and identifying chemical substances or compounds, in particular of explosive and/or unhealthy substances or compounds to be detected at very low concentrations.

The detection of explosive and/or toxic chemical compounds requires measurement methods with detection limits in the ppt-ppb range. Spectrometers are frequently used for detecting and identifying these chemical compounds. Preferred is the use of ion mobility spectrometer (IMS), also referred to as plasma chromatographs, because they do not require, unlike other spectrometers, such as a mass spectrometer, a vacuum pump for generating a vacuum for detecting chemical substances or compounds. IMS therefore have a small footprint and an inexpensive construction compared to other spectrometers.

IMS are used in a large number of applications, ranging from the medical field, for example when examining the air exhaled by patients, the use in production monitoring, e.g. in quality control of food items, to the military field, e.g. for detecting chemical warfare agents. A general overview of IMS and their applications can be found, for example, in: G. A. Eiceman and Z. Karpas "Ion Mobility Spectrometry" (2nd. edition, CRC, Boca Raton, 2005).

The structure and the operation of the IMS have been described in various publications.

For example, U.S. Pat. No. 3,621,240 discloses a classic time-of-flight IMS, utilizing the different mobility of ions at atmospheric pressure. The target compounds are hereby continuously ionized in an ion source either by using radioactive radiation, photo ionization or corona discharges. Frequently, radioactive sources are used which ionize the air molecules directly. These ionized air molecules react further and form together with water molecules reactant ions. These reactant ions react via proton transfer, electron transfer or proton abstraction reactions with the compounds of interest and form the so-called product ions. These product ions are introduced within a very short time span of about 200 microseconds into a drift tube with the aid of an electric grid, which has an electric field and accelerates the ions in a drift gas, typically filtered air, at ambient pressure. Positive ions can be detected in a positive operating mode and negative ions in a negative operating mode by changing the polarity of the electric field of the drift region. The introduced product ions are continuously accelerated by the electric field and continuously decelerated as a result of collisions with the neutral molecules in the drift gas. The electric field exerts an identical pulling force on all ions having the same charge. However, the product ions have different drift velocities due to their different diameters and shapes. At the end of the drift tube, the product ions impinge on a detector with these different drift velocities. From the different times-of-flight of the product ions through the drift tube, which are typically in the range 5 to 30 milliseconds, conclusions can be drawn with respect to the different examined chemical compounds.

The switching process of the electric grid, which lets only a portion of the ions pass into the drift space, defines a starting pulse for the measurement of the drift velocity in classical time-of-flight IMS. The introduced ions diffuse broadly due to the collisions with the molecules of the ambient air. The signal measured at the detector is therefore in the shape of a Gaussian bell curve. The drift velocity can be determined from the measured time-of-flight or from the drift time at the maximum of the bell-shaped curve and the known length of the drift region, wherein a resulting spectrum can be used to identify the chemical substances or compounds.

The time-of-flight of the product ions through the drift tube is inversely proportional to the drift velocity, with which the product ions strike the detector. The drift velocity depends in turn on the ion mass and the size and shape of the ions, respectively, as a result of the acceleration in the electric field and the deceleration due to collisions of ions with the neutral molecules.

The drift velocity of the product ions $v_d$ depends linearly on the field strength at a small field strength E, e.g. E=200 V/cm. The mobility K of the product ions is at these small field strengths then independent of the field strength and can be expressed as follows:

$$K=v_d/E.$$

Because the drift velocity of the ions depends also on the temperature and the pressure in the drift tube, the mobilities of the product ions for identifying and detecting the chemical compounds are always referenced to standard conditions, i.e. standard temperature $T_0$=273 K and standard pressure $P_0$=1013 hPa. The reduced or normalized mobilities of the product lines can then be expressed as follows:

$$K_0=K\cdot(T_0/T)\cdot(p/p_0)=K\cdot(273\ K/T)\cdot(p/1013\ hPa).$$

Disadvantageous, however, when using the classical time of flight IMS, only a small portion, typically 1%, of the product ions is used for the detection and hence evaluation of the tested chemical compounds. Because the starting pulse of the electric grid is relatively short compared to the drift time of the ions, only a small portion, typically 1%, of the product lines passes through the grid and enters the drift tube. The majority of the product ions strike the grid when the grid is closed and are thus neutralized on the grid.

The yield of the product ions reaching the drift the tube can be optimized and thereby the detection limit of the tested chemical substances or compounds can be increased by increasing the ion throughput in combination with modulation of the ion beam with barrier grids. For example, such modulation of the ion current is proposed in DE 195 15 270 C2, which allows the time-of-flight spectrum of the IMS to be computed with a mathematical deconvolution, for example by applying a Hadamard or Fourier transformation.

The aforedescribed IMS, however, has the disadvantage that only positive or only negative product ions can be measured, requiring the polarity of the separation tube to be changed, which lengthens the duration of the measurement.

It is therefore desirable to operate two drift tubes in parallel so as to be able to measure both positive and negative product ions from one and the same sample. For example, an ion mobility detector is proposed in U.S. Pat. No. 4,445,038 which includes two drift tubes, one each for positive and negative product ions, with each drift tube including an electric grid. However, the opposing arrangement of the two drift tubes is here disadvantageous. According to Rokushika, Hatano, Baim and Hill [Rokushika S., Hatano H., Baim M. A., Hill H. H., Resolution Measurement for Ion Mobility Spectrometry, Anal. Chem. 1985, 57, 1902], the resolution of an IMS is proportional to the analyzing time. To attain the best possible resolution, it is therefore desirable to construct the drift tubes as long as possible. Especially mobile devices become too large and too unwieldy with the arrangement proposed in U.S. Pat. No. 4,445,038.

It is therefore the object of the invention to develop a generic method for identifying gases as well as an associated device which has a compact construction and allows an immediate and simultaneous detection of the chemical compounds to be tested and simultaneously allows a more efficient utilization of the product ions available for detection.

This object is attained with the invention by a method having the features recited in claim 1 and by a device having the features recited in claim 3, as well as by a device having the features recited in claim 10. Preferred embodiments are recited in the dependent claims 2 and 4 to 9.

The method according to the invention for identifying gases as well as the associated devices eliminate the aforementioned disadvantages of the prior art.

With the novel method for identifying gases, both positive and negative product ions can advantageously be detected in parallel and concurrently, which can be achieved in a very small space. Advantageously, the sample to be measured may be introduced into the ionizing region by way of a carrier gas flow, where positive and negative product ions are formed by direct ionization or charge transfer reactions. It is particularly advantageous when the product ions are separated by electric fields according to their polarity and transported to the front of the inlet region of the respective corresponding drift spaces without entering the drift spaces. According to another particular advantage, electric fields may be switched off in a pulse-like fashion, and additional electric fields may be switched on in a pulse-like fashion, whereby 100% of the product ions are injected at the start time into their respective drift space. The product ions present in the drift space are advantageously accelerated toward the detector by another constant electric field. A constant drift velocity is attained as a result of the constant collisions with the molecules of the drift gas. After passing through the shielding grid in the immediate vicinity of the detectors, the product ions are captured on the respective detector, transported to the transimpedance amplifier as a current and converted into measurable voltages. Depending on the time of impact on the detector, a characteristic drift time can be assigned to each sample. Advantageously, for evaluating the measured drift times and for identifying the chemical compounds, these measured drift times are compared with previously determined drift times of known chemical compounds and/or the measured drift times are compared with the known drift times of substances and compounds by using mathematical or statistical methods, for example rule-based algorithms or artificial neural networks.

Advantageously, in the application of the new device for identifying gases, both drift tubes may be, on one hand, delimited by a common inlet system and, on the other hand, by a respective detector. An electrode arrangement dividing the drift tubes into a corresponding reaction chamber and two drift spaces is disposed in each drift tube, wherein an ion source is arranged in the common reaction chamber and a corresponding shielding grid is arranged in each of the drift chambers. Advantageously, the drift spaces may be constructed from alternatingly arranged metal rings and insulator rings, wherein each metal ring forms a respective DC voltage electrode around the drift space, or the drift spaces are each composed of one or more tubes having a low electrical conductivity. In a particularly advantageous embodiment, both drift spaces may be arranged in parallel next to one another and operated with opposite voltages applied in the region of the detector and producing the electric field.

The object is also attained with a device for introducing ions into a drift space of an ion mobility spectrometer, which includes a first electrode arrangement for separating positive and negative product ions from an accumulation of product ions inside a reaction chamber and a second electrode arrangement for accelerating the positive or negative product ions into the drift space. In this way, an electrical grid for admitting product ions into the drift space can advantageously be eliminated. Controllable electrode arrangements are used to separate the positive or negative product ions, as well as to subsequently accelerate the separated product ions into the drift space. The start pulse for measuring the drift velocity inside to drift space can be generated at the same time by appropriate control. This approach significantly simplifies the structure of the ion mobility spectrometer and enables a more effective operation. The device can be used with both single tube mobility spectrometers as well as with ion mobility spectrometers having two or more drift tubes.

The method of the invention for identifying gases and the associated device can be realized in various ways. The invention will now be explained further with reference to an exemplary embodiment, wherein:

FIG. 1 shows a schematic diagram of an ion mobility spectrometer.

The device for identifying gases, generally designated with the reference numeral 100, is according to the exemplary embodiment composed of two drift tubes 19 and 20 which are delimited, on one hand, by an inlet system 1 and, on the other hand, by two detectors 9 and 10 constructed from a planar conductive plate.

Ion guide electrodes 3, 4, 5 and 6 are disposed in the drift tube 19 and 20, thereby dividing the interior space of the drift tubes 19 and 20 into a common reaction chamber 26 and two drift spaces 24 and 25. The reaction chamber 26 is delimited by the inlet system 1, whereas the drift spaces 24 and 25 are delimited by the detectors 9 and 10. Moreover, an ion source 2 is arranged in the reaction chamber 26 near the inlet system 1, and a respective shielding grid 7 and 8 is arranged in the drift spaces 24 and 25 in front of each detector 9 and 10, wherein the ion source 2 has a radioactive Ni63 foil and the shielding grids 7 and 8 are used for capacitive decoupling.

The ion guide electrodes 3, 4, 5 and 6 in the reaction chamber are planar electrodes disposed on the sides that delimit the reaction chamber 26.

Drift electrodes 22 and 23, which are electrically interconnected t by resistors and form DC voltage electrodes, are arranged in the drift spaces 24 and 25. The voltages applied to the drift electrodes 22 and 23 are selected so as to generate constant field strengths in the drift spaces 24 and 25.

The device 100 for identifying gases has the following function: The chemical compound to be tested, including the ambient air, is transported via the inlet system 1 by a carrier gas flow into the ion source 2. The inlet system 1 may be constructed as a small opening or for mobile systems from a silicone membrane.

Primarily air molecules from the ambient air are ionized in the ion source 2 by the radioactive radiation of the Ni63 foil. So-called reactant ions are formed by additional reactions and deposits with water molecules. These reactant ions then react with the molecules of the chemical compounds to be tested by way of proton transfer reactions, electron transfer reactions or proton abstraction reactions, forming product ions. The thereby produced positive and negative product ions enter an electric field produced by the ion guide electrodes 3 and 6; the product ions are separated according to their polarity by opposite voltages applied at the ion guide electrodes 3 and 6 in front of the respective corresponding drift space 24 and 25, respectively, but without entering the drift space. In this state, no product ions are present in the two drift spaces 24 and 25.

The product ions are injected into the drift space 24 and 25, respectively, by switching off the voltages at the ion guide electrodes 3 and 6 and hence also the generated electric field and by simultaneously switching on voltages at the ion guide electrodes 4 and 5 which are polarized such that the product ions located in front of the ion guide electrodes 4 and 5 are repelled, thus starting the time-of-flight measurement. All product ions residing at this time in front of the respective drift space 24 and 25 are injected into the drift space. The product ion injection process is terminated by reversing the above process, i.e. by turning off the voltages at the ion guide electrodes 4 and 5 and turning on the voltages at the ion guide electrodes 3 and 6, with more product ions moving again in front of the respective drift space without entering the drift space. This process repeats periodically, so that sample gases can be measured continuously, wherein the positive and negative product ions are measured simultaneously and are introduced more efficiently into the drift spaces 24 and 25

Each of the voltages at the drift electrodes 22 and 23 generates a corresponding electric field which accelerates positive and/or negative charge carriers towards the detector. The product ions now residing in the drift spaces 24 and 25 are captured by this electric field and pulled toward detector 9 and 10. On the way to the detectors 9 and 10, the ions must pass through the electric fields generated by the drift electrodes 22 and 23, wherein these electrical fields exert the same pulling force on all ions of identical charge. Because the ions collide constantly with the neutral air molecules, the velocity of the ions in the electric fields depends on the ion mass and the ion size, respectively, and the ion shape. The electric fields with a low field strength generated by the drift electrodes 22 and 23 cause ions of identical diameter and shape to be accelerated to identical drift velocities and ions with different diameters and shapes to be accelerated to different drift velocities.

The ions strike the detectors 9 and 10 at the end of drift chambers 24 and 25. The detectors 9 and 10 are Faraday collectors, wherein the shielding grids 7 and 8 arranged in front of the detectors 9 and 10 are used for capacitive decoupling between the product ions located just before the detectors 9 and 10 and the detectors 9 and 10

The measurement signals from the detectors 9 and 10 are evaluated in a control unit 21, wherein the drift times of the product ions through the drift spaces 24 and 25 are determined from the injection process and the impact of the ions on the detectors 9 and 10. This determination can be performed because the control unit also controls the ion guide electrodes 3, 4, 5 and 6. The measured drift times are evaluated by comparing them with previously determined drift times of known chemical compounds, wherein for identical drift times also identical product ions, and thus identical chemical compounds are present.

It would also be feasible to replace the conversion processes occurring in the ion source 2 by other suitable processes. For example, the ions could also be generated through photoionization or corona discharges instead of radioactive radiation.

It would also be feasible to optimize the selectivity of the drift tubes 19 and 20 by using an additional reaction gas or dopant gas. This reaction gas can be used to affect chemical reactions, which are controlled, for example, by proton affinities for negative ions and by electronegativities for negative ions, so that the selectivity of the process can be influenced. In addition, the selectivity of the drift tube 19 and 20 can also be affected by addition processes and deposition processes of the reaction gases or of other electrically neutral gases on the ions at high field strengths.

Furthermore, the ion mobility spectrometer can also be combined with other sensors or detectors and/or with other methods for increasing the selectivity, in particular with an upstream gas chromatograph.

LIST OF REFERENCE SYMBOLS

1 Inlet system
2 Ion source
3 Electrode ion guide
4 Electrode ion guide
5 Electrode ion guide
6 Electrode ion guide
7 Shielding grid
8 Shielding grid
9 Detector
10 Detector
11 Drift gas inlet
12 Drift gas outlet
13 Drift gas inlet
14 Drift gas inlet
15 Drift gas outlet
16 Drift gas inlet
17 Pump
18 Pump
19 Drift tube
20 Drift tube
21 Controller
22 Drift electrode
23 Drift electrode
24 Drift space
25 Drift space
26 Reaction chamber
100 Device

The invention claimed is:

1. A device for identifying gases, which comprises at least two drift tubes, wherein each of the drift tubes has at least one detector for detecting product ions, wherein at least two drift tubes are arranged in parallel with each other and are delimited, on one hand, by a common intake system and, on the other hand, by at least one detector, whereint he two drift tubes are defined at least in part by an ion guide electrode arrangement, which defines a common reaction chamber with a single ion source disposed in the common reaction chamber and a respective shielding grid is disposed ine ach of the drift spaces.

2. A method for identifying gases, wherein the gases to be identified are ionized and the drift times of the positive and negative product ions through drift spaces are measured and the measured drift times are evaluated, wherein for measuring the drift times the product ions are accelerated to drift velocities by a resulting electrical field, wherein the positive and negative product ions move synchronously and in parallel in the same direction.

3. The method of claim 1, wherein the product ions are injected into the drift spaces perpendicular to their preferred direction.

4. The device according to claim 1, wherein the drift spaces comprise alternatingly arranged drift electrodes, wherein each drift electrode is electrically connected around the drift spaces and forms a respective DC voltage electrode.

5. The device according to claim 1, wherein the drift spaces are composed of one or more tubes having a low electrical conductivity.

6. The device according to claim 1, wherein the ion guide electrodes are planar and form the boundary of the reaction chamber.

7. The device according to claim 1, wherein two switching states can be realized with the ion guide electrodes, wherein:
   in a first switching state, the product ions are moved by an electric field in front of the respective corresponding drift spaces, without allowing the product ions to enter the drift spaces, and
   in a second switching state, the product ions are injected into the corresponding drift spaces by switching off the voltages at the ion guide electrodes and hence also the driving electric field, and by simultaneously switching on the voltages at the ion guide electrodes.

8. The device according to claim 6, wherein the shielding grids are arranged in front of the detectors, wherein the shielding grids are used for capacitive decoupling.

* * * * *